United States Patent
Chen et al.

(10) Patent No.: US 6,997,959 B2
(45) Date of Patent: Feb. 14, 2006

(54) MULTI-FUNCTIONAL ARTIFICAL KNEE JOINT

(76) Inventors: Chien-Liang Chen, 7F, No. 136, Sec. 2, Ho-Ping W. Rd., Taipei City (TW); Chien-Chuan Chen, 7F, No. 136, Sec. 2, Ho-Ping W. Rd., Taipei City (TW); I-Chun Chen, 7F, No. 136, Sec. 2, Ho-Ping W. Rd., Taipei City (TW)

(*) Notice: Subject to any disclaimer, the term of this patent is extended or adjusted under 35 U.S.C. 154(b) by 364 days.

(21) Appl. No.: 10/631,739

(22) Filed: Aug. 1, 2003

(65) Prior Publication Data

US 2005/0027370 A1   Feb. 3, 2005

(51) Int. Cl.
*A61F 2/64* (2006.01)
*A61F 2/74* (2006.01)
(52) U.S. Cl. ............................. 623/26; 623/43; 623/44; 188/313; 188/322.13
(58) Field of Classification Search .................. 623/26, 623/39, 40, 41, 42, 43, 44, 45, 46; 188/313, 188/322.13
See application file for complete search history.

(56) References Cited

U.S. PATENT DOCUMENTS

| 5,904,721 A | * | 5/1999 | Henry et al. | 623/26 |
| 6,117,177 A | * | 9/2000 | Chen et al. | 623/44 |
| 6,558,430 B1 | * | 5/2003 | Nakaya et al. | 623/44 |
| 6,706,074 B1 | * | 3/2004 | Chen | 623/44 |

FOREIGN PATENT DOCUMENTS

WO   WO 9222267 A1  * 12/1992

* cited by examiner

*Primary Examiner*—David H. Willse
*Assistant Examiner*—Javier G. Blanco
(74) *Attorney, Agent, or Firm*—Foley & Lardner LLP

(57) ABSTRACT

An artificial knee joint connects a prosthetic lower leg to a residual thigh of a prosthesis wearer, and includes a knee-extending oil passage and a knee-flexing oil passage that is provided with a throttle valve. When the lower leg is pressed against the ground by the thigh, a controlling element activates the throttle valve to close the knee flexing oil passage so as to fix the thigh relative to the lower leg. Upon fast walking of the wearer, an air valve unit activates the throttle valve to reduce flow rate of oil flowing through the knee-flexing oil passage so that the lower leg can support the thigh effectively.

8 Claims, 8 Drawing Sheets

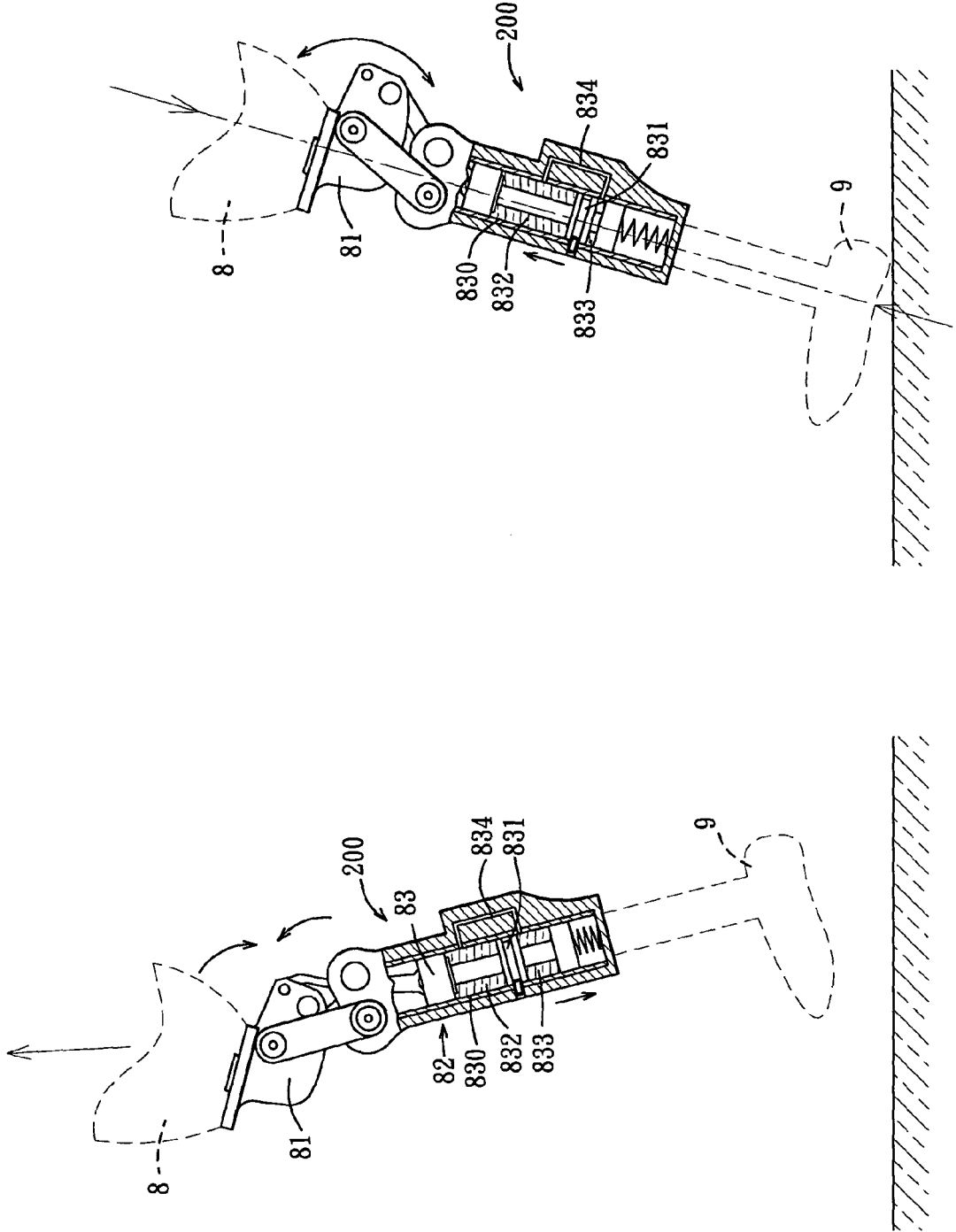

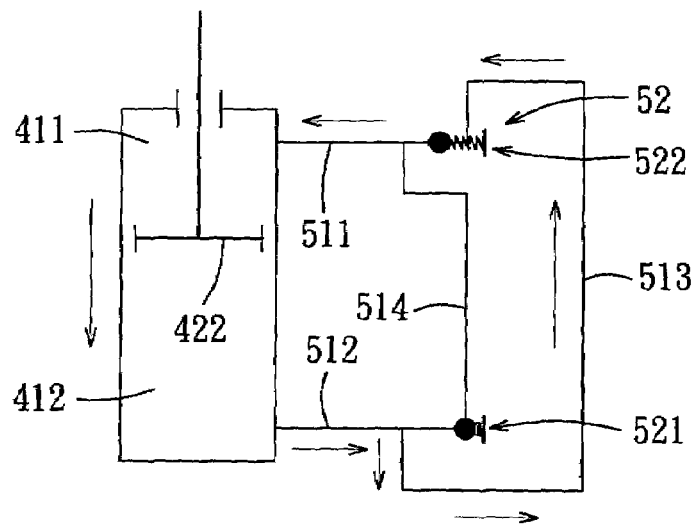
FIG. 8
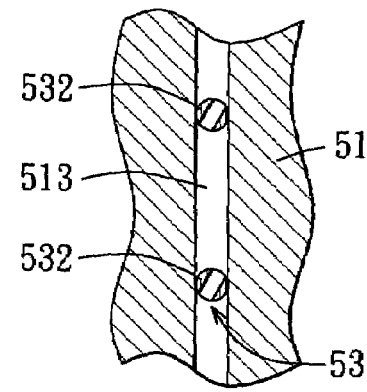
FIG. 10
FIG. 9

MULTI-FUNCTIONAL ARTIFICAL KNEE JOINT

BACKGROUND OF THE INVENTION

1. Field of the Invention

This invention relates to an artificial knee joint, and more particularly to a multi-functional artificial knee joint that is suitable for fast and slow walking on sloping paths.

2. Description of the Related Art

Referring to FIGS. 1 and 2, a conventional artificial knee joint 200 is shown to include a linkage unit 81, a support frame 82 connected to a residual thigh 8 of a prosthesis wearer by the linkage unit 81, and a hydraulic device 83. The hydraulic device 83 includes a cylinder body 830, and a piston 831 disposed movably within the cylinder body 830 and connected to the linkage unit 81 so as to divide an interior space in the cylinder body 830 into upper and lower oil chambers 832, 833, which are communicated by an oil passage 834. When the thigh 8 is raised such that the joint 200 flexes to form an angle between the thigh 8 and a prosthetic lower leg 9, as shown in FIG. 1, the piston 831 moves from an upper limit position to a lower limit position.

When the lower leg 9 is aligned with the thigh 8 and is pressed against the ground by the thigh 8, as shown in FIG. 2, the piston 831 moves from the lower limit position to the upper limit position. Although the aforesaid conventional artificial knee joint can flex and extend, the lower leg 9 cannot provide a sufficient support to the thigh 8 during fast walking of the wearer or during walking of the wearer along a sloping path.

SUMMARY OF THE INVENTION

It is the object of this invention to provide a multi-functional artificial knee joint that is suitable for fast and slow walking on a sloping path.

According to this invention, an artificial knee joint connects a prosthetic lower leg to a residual thigh of a prosthesis wearer, and includes a knee-extending oil passage and a knee-flexing oil passage that is provided with a throttle valve. When the lower leg is pressed against the ground by the thigh, a controlling element activates the throttle valve to close the knee flexing oil passage so as to fix the thigh relative to the lower leg. As such, when the joint flexes and when the lower leg stands on a sloping path, the lower leg can provide a sufficient support to the thigh. Upon fast walking of the wearer, an air valve unit activates the throttle valve to reduce flow rate of oil flowing through the knee-flexing oil passage so that the flex angle of the joint is reduced, thereby facilitating fast walking of the wearer.

BRIEF DESCRIPTION OF THE DRAWINGS

These and other features and advantages of this invention will become apparent in the following detailed description of a preferred embodiment of this invention, with reference to the accompanying drawings, in which:

FIG. 1 is a schematic sectional view of a conventional artificial knee joint, illustrating the flexion of the joint;

FIG. 2 is a schematic sectional view of the conventional artificial knee joint, illustrating full extension of the joint;

FIGS. 8 and 9 are schematic fragmentary views of the preferred embodiment, illustrating operation of a control valve unit;

FIG. 10 is a schematic fragmentary view of the safety device of the preferred embodiment, illustrating upper and lower first throttle valves are disposed in a knee-flexing oil passage;

DETAILED DESCRIPTION OF THE PREFERRED EMBODIMENT

Figure 3:
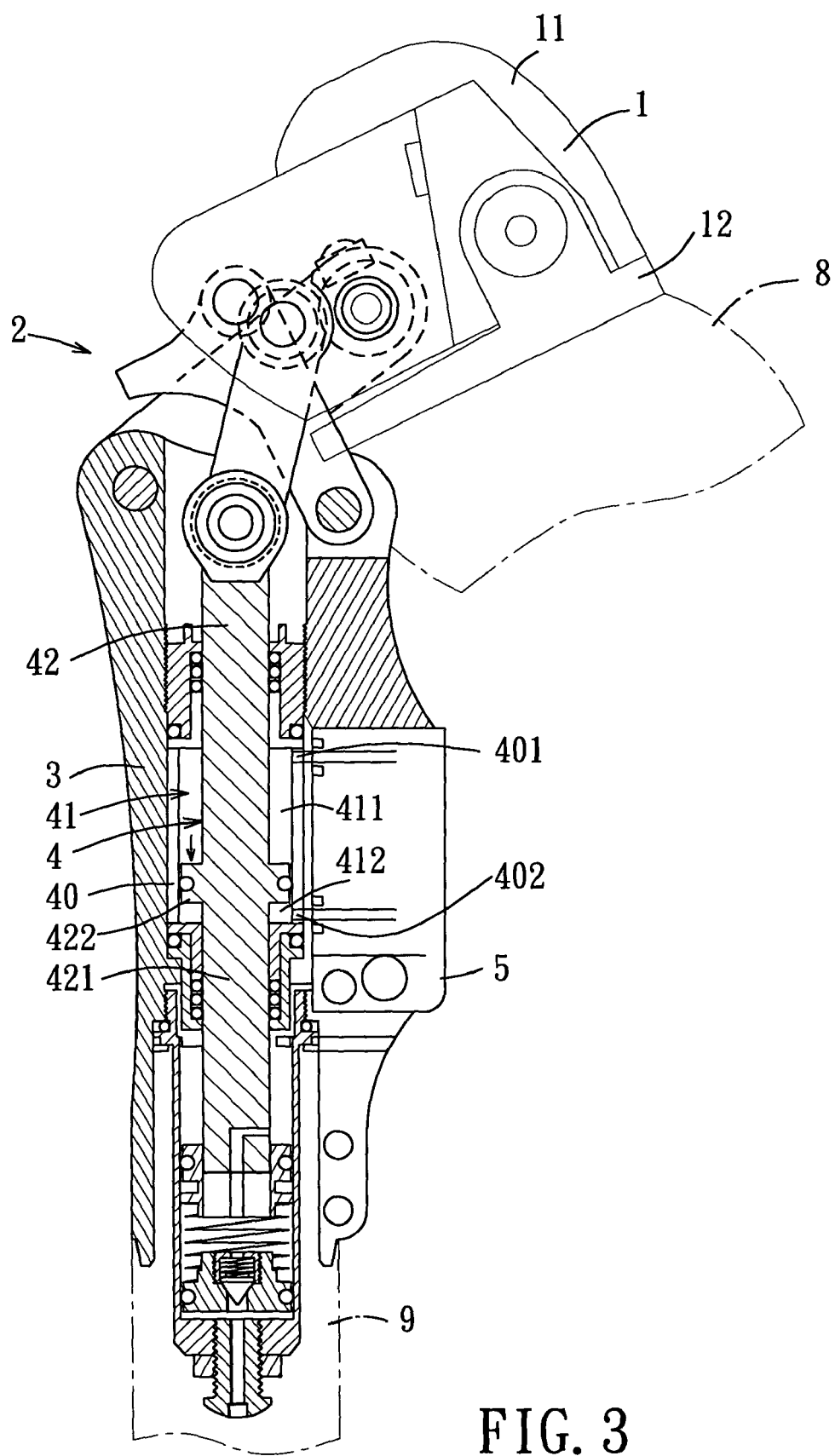
FIG. 3 is a schematic sectional view of the preferred embodiment of a multi-functional artificial knee joint according to this invention, illustrating how the joint flexes to move a piston to an upper limit position.
Figure 4:
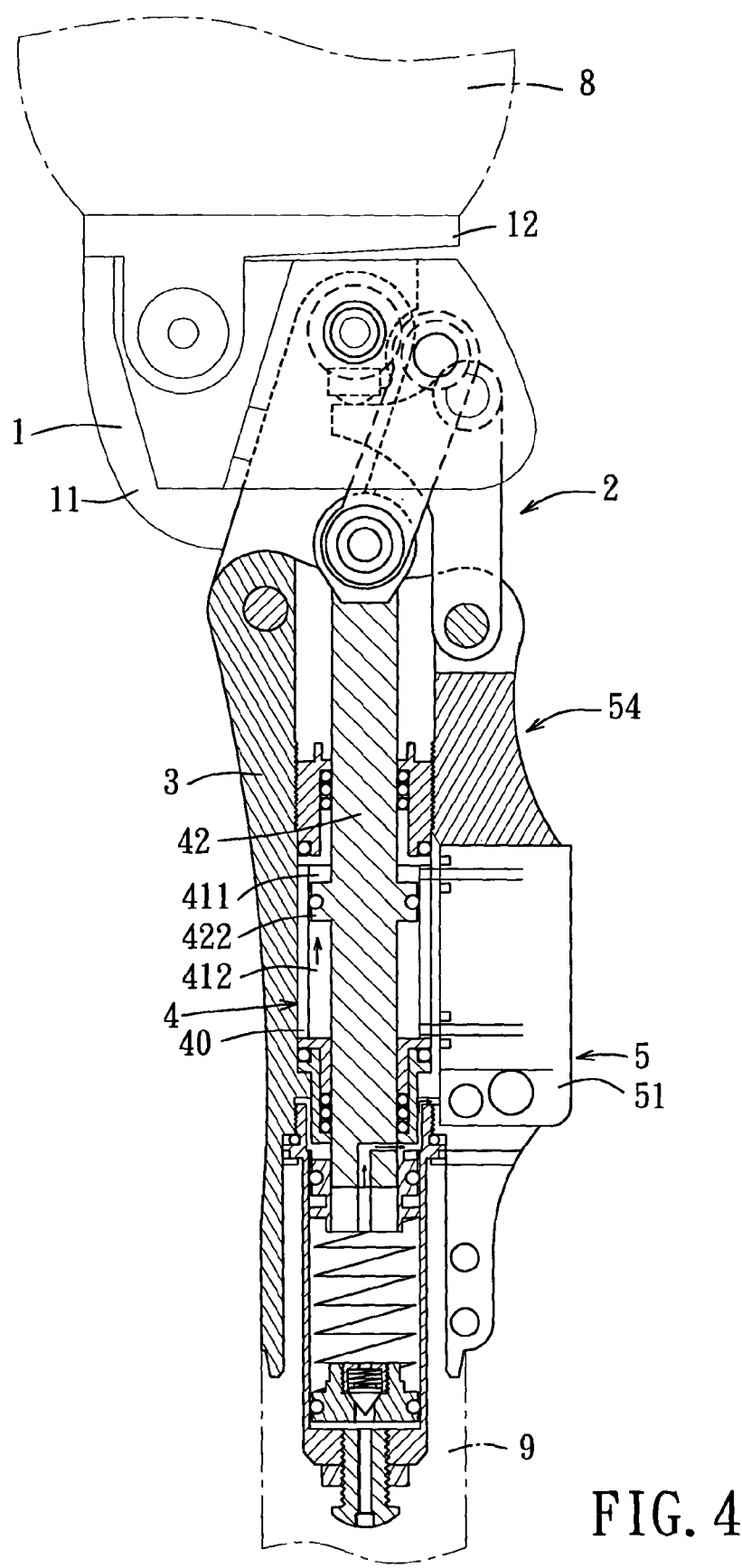
FIG. 4 is a schematic sectional view of the preferred embodiment, illustrating how the joint extends to move a piston to a lower limit position.

Referring to FIGS. 3 and 4, the preferred embodiment of a multi-functional artificial knee joint according to this invention is shown to include a joint seat 1, a first linkage unit 2, a hollow support frame 3, a hydraulic device 4, and a safety device 5.

The joint seat 1 has a joint body 11, and a rotatable member 12 connected pivotally to the joint body 11 and connected fixedly to a sleeve (not shown) that is connected fixedly to a residual thigh 8 of a prosthesis wearer.

The first linkage unit 2 is connected to the joint body 11 and the support frame 3 in a known manner.

The hydraulic device 4 is disposed within the support frame 3, and includes a cylinder body 40 with an interior space 41, and a piston unit 42 that consists of a piston rod 421 and a piston 422 connected fixedly to the piston rod 421 and disposed slidably within the cylinder body 40 so as to divide the interior space 41 in the cylinder body 40 into an upper oil chamber 411 and a lower oil chamber 412. The cylinder body 40 is formed with an upper opening 401 in fluid communication with the upper oil chamber 411, and a lower opening 402 in fluid communication with the lower oil chamber 412. The piston 422 is driven by the first linkage unit 2 to move within the cylinder body 40 between an upper limit position shown in FIG. 4 and a lower limit position shown in FIG. 3. When the joint flexes to form an angle between the thigh 8 and a prosthetic lower leg 9, the piston 422 moves from the upper limit position to the lower limit position. When the joint extends to align the thigh 8 with the lower leg 9, the piston 422 moves from the lower limit position to the upper limit position.

Figure 6:
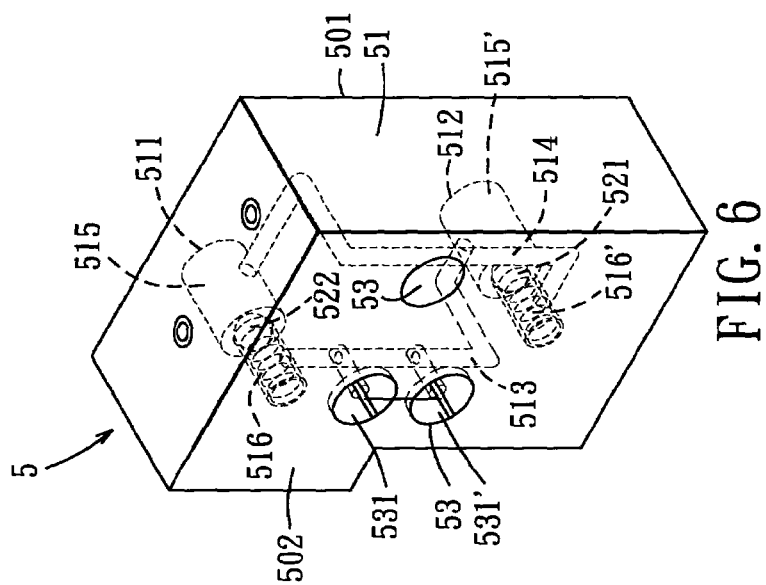
FIG. 6 is a perspective view of a main body of the safety device of the preferred embodiment.
Figure 5:
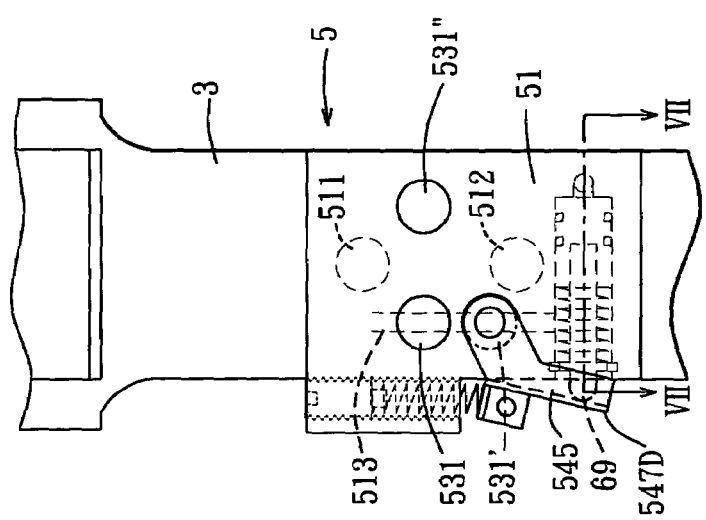
FIG. 5 is a rear view of a safety device of the preferred embodiment.

Referring to FIGS. 4, 5, and 6, the safety device 5 includes a main body 51, a control valve unit 52, an adjustment unit 53, and a second linkage unit 54.

The main body 51 has a first side surface 501 and a second side surface 502 that are opposite to each other. The first side surface 501 is formed with an upper opening 511 that is in fluid communication with the upper oil chamber 411 through the upper opening 401 in the cylinder body 40. The second side surface 502 is formed with a lower opening 512 that is in fluid communication with the lower oil chamber 412 through the lower opening 402 in the cylinder body 40. The main body 51 further has a knee-flexing oil passage 513 and a knee-extending oil passage 514, each of which is in fluid communication with the upper and lower oil chambers 411, 412. Each of the upper and lower openings 511, 512 has a large-diameter portion 515, 515', and a small-diameter portion 516, 516'. The knee-flexing oil passage 513 has an upper end that is in fluid communication with the small-diameter portion 516 of the upper opening 511, and a lower end that is in fluid communication with the large-diameter portion 515' of the lower opening 512. The knee-extending oil passage 514 has an upper end that is in fluid communication with the large-diameter portion 515 of the upper opening 511, and a lower end that is in fluid communication with the small-diameter portion 516' of the lower opening 512. An air inlet 517 is formed in the first side surface 501 of the main body 51. An air outlet 518 is formed in an upper end portion of the main body 51, and is in fluid communication with the air inlet 517 through an air passage 519.

Referring to FIGS. 6, 8, and 9, the knee-flexing oil passage 513 and the knee-extending oil passage 514 are communicated with the upper opening 511 at upper ends thereof, and with the lower opening 512 at lower ends thereof. The control valve unit 52 includes a spring-biased first unidirectional valve 521 disposed in the knee-extending oil passage 513 for preventing oil flow from the lower oil chamber 412 into the upper oil chamber 411 through the knee-extending oil passage 513 and for permitting oil flow from the upper oil chamber 411 into the lower oil chamber 412 through the knee-extending oil passage 514, and a spring-biased second unidirectional valve 522 disposed in the knee-flexing oil passage 513 for preventing oil flow from the upper oil chamber 411 into the lower oil chamber 412 through the knee-flexing oil passage 513 and for permitting oil flow from the lower oil chamber 412 into the upper oil chamber 411 through the knee-flexing oil passage 513. Each of the first and second unidirectional valves 521, 522 includes a coiled compression spring disposed in a corresponding one of the small-diameter portions 516', 516 of the lower and upper openings 512, 511, and a ball disposed at a shoulder defined between the small-diameter portion 516', 516 and the large-diameter portion 515', 515 of a corresponding one of the lower and upper openings 512, 511. As such, upon flexion of the joint, the piston 422 moves downward so as to force oil to flow from the lower oil chamber 412 into the upper oil chamber 411 through the upper and lower openings 511, 512 and the knee-flexing oil passage 513, as shown in FIG. 8. Upon extension of the joint, the piston 422 moves upward so as to force oil to flow from the upper oil chamber 411 into the lower oil chamber 412 through the upper and lower openings 511, 512 and the knee-extending oil passage 514, as shown in FIG. 9.

Referring to FIGS. 6 and 10, the adjustment unit 53 includes a pair of upper and lower first throttle valves 531, 531' (see FIG. 5) that are disposed in the knee-flexing oil passage 513. Each of the upper and lower first throttle valves 531, 531' is configured as an adjustment bolt that has an inner end portion 532 which extends into the knee-flexing oil passage 513. The upper and lower first throttle valves 531, 531' can be rotated to adjust the volumes of the inner end portions 532 extended into the knee-flexing oil passage 513 so as to regulate oil flow in the knee-flexing oil passage 513. The adjustment unit 53 further includes a throttle valve 53" (see FIGS. 5, 11, and 13) that has the same structure as the upper and lower first throttle valves 531, 531'.

Figure 11:
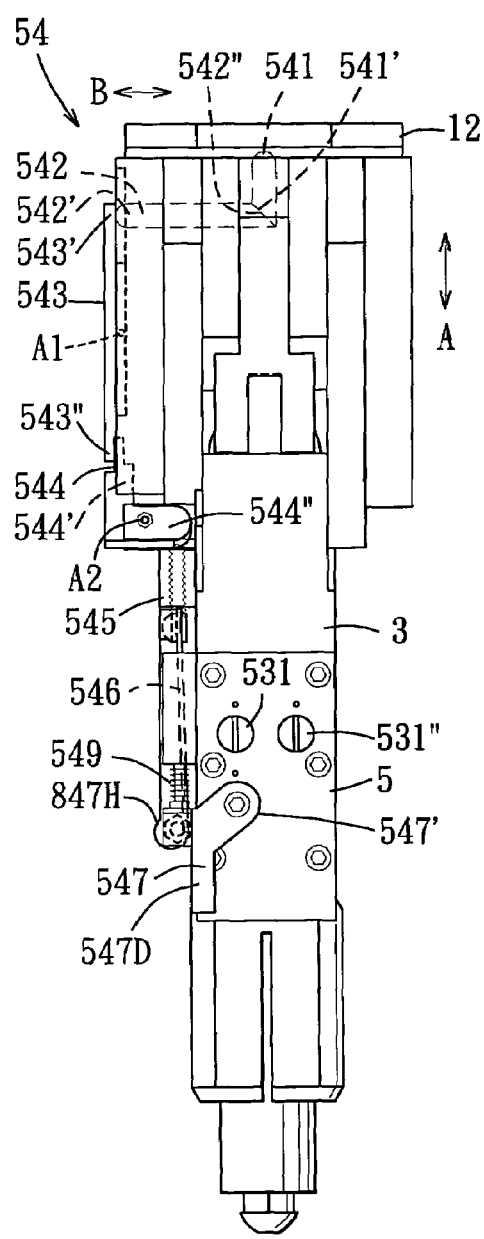
FIGS. 11 and 12 are schematic rear and side views of the preferred embodiment, illustrating how a controlling element is disposed at an extended position, where oil can flow through the knee-flexing oil passage.
Figure 12:
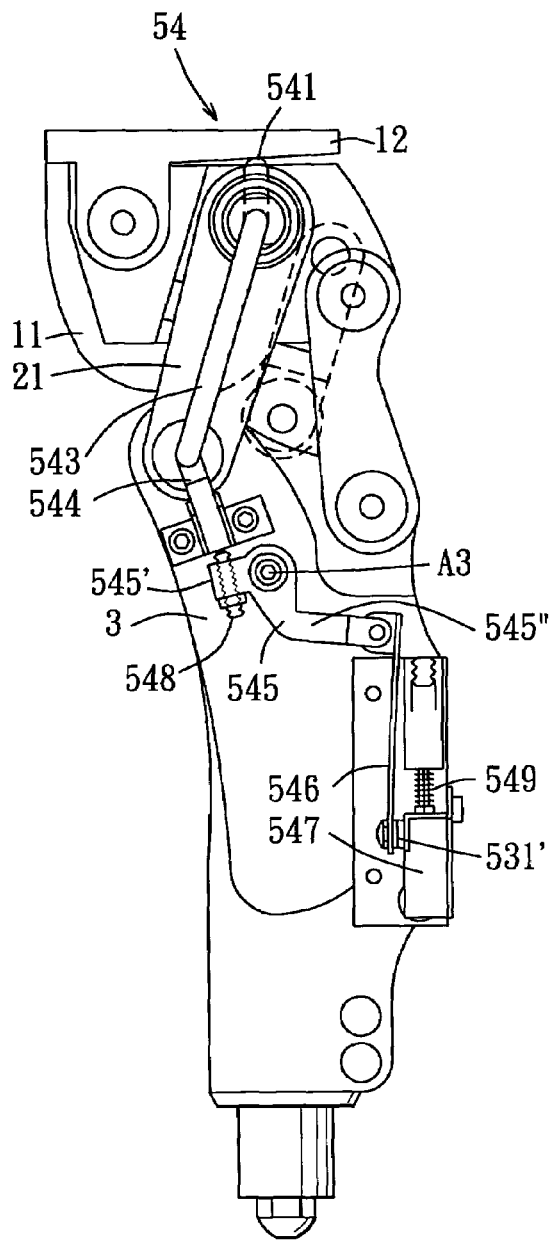
Figure 13:
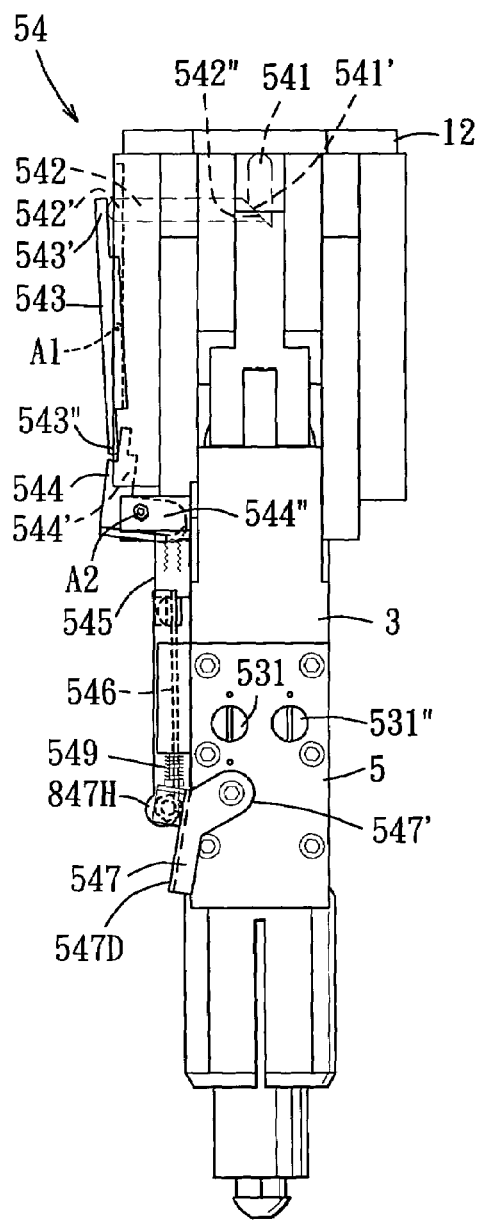
FIGS. 13 and 14 are schematic rear and side views of the preferred embodiment, illustrating how the controlling element is pressed by a rotatable member to stop the oil flow through the knee-flexing oil passage.
Figure 14:
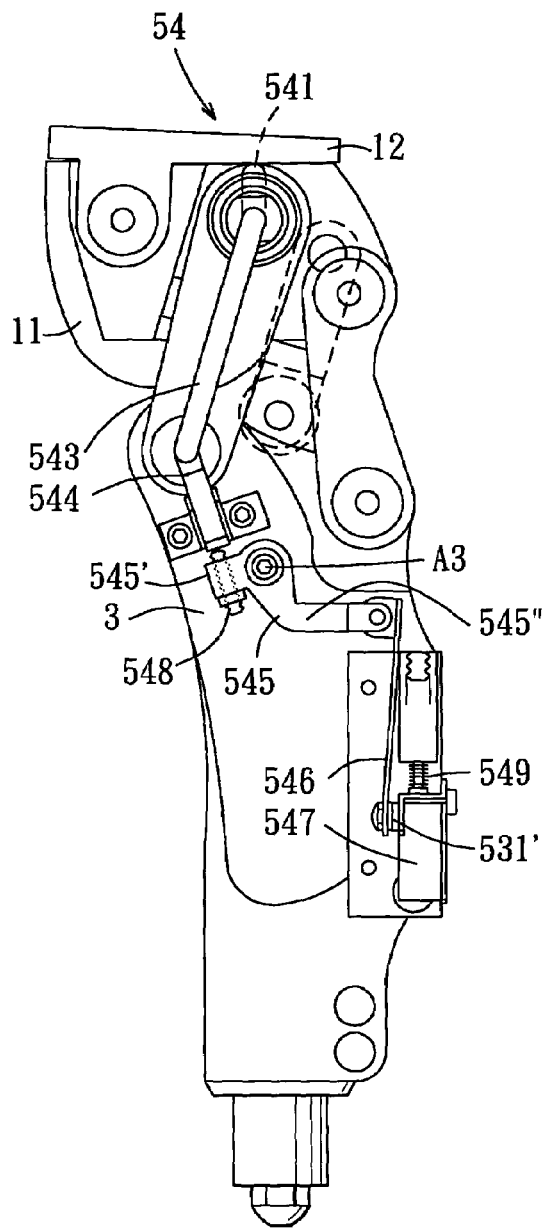
Figure 15:
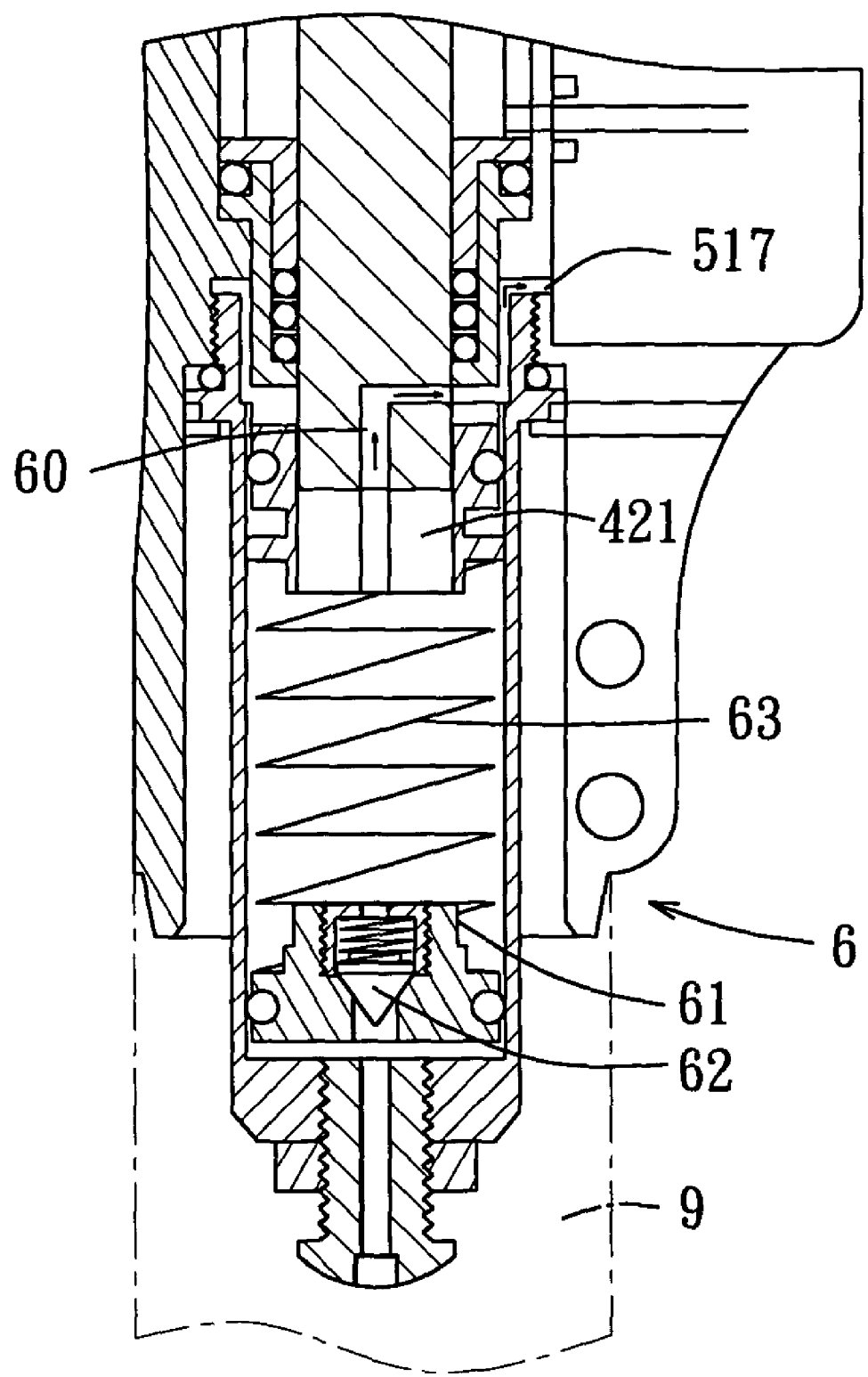
FIG. 15 is a schematic fragmentary sectional view of the preferred embodiment, illustrating how an air valve unit is connected to a hydraulic device.

Referring to FIGS. 6, 11, and 12, the second linkage unit 54 connects the lower first throttle valve 531' to a controlling element 541 that is configured as a vertical sliding rod which is guided to move along a longitudinal direction (A) (see FIG. 11) of the support frame 3 between an extended position shown in FIGS. 11 and 12, and a retracted position shown in FIGS. 13 and 14, and which has an inclined lower end surface 541'. The second linkage unit includes a horizontal sliding rod 542, a vertical swing lever 543, a generally L-shaped crank member 544, a generally Z-shaped crank member 545, a vertical link 546, and a swing arm 547.

The horizontal sliding rod 542 is disposed movably within the support frame 3, and has an outer end 542' and an inclined inner end surface 542" that is biased to press horizontally against and that is slidable on the inclined lower end surface 541' of the controlling element 541. The horizontal sliding rod 542 is guided to move along a transverse direction (B) (see FIG. 11) of the support frame 3 between a non-pushing position shown in FIGS. 11 and 12, where the controlling element 541 is disposed at the extended position, and a pushing position shown in FIGS. 13 and 14, where the controlling element 541 is disposed at the retracted position.

The vertical swing lever 543 has a middle portion mounted pivotally on the support frame 3, an upper end portion 543' biased to press against the outer end 542' of the horizontal sliding rod 542, and a lower end portion 543", and is rotatable about a first horizontal axis (A1) between a vertical position shown in FIGS. 11 and 12, where the horizontal sliding rod 542 is disposed at the non-pushing position, and an inclined position shown in FIGS. 13 and 14, where the horizontal sliding rod 542 is disposed at the pushing position. The first horizontal axis (A1) is perpendicular to the controlling element 541 and the horizontal sliding rod 52.

The L-shaped crank member 544 is mounted pivotally on the support frame 3, is rotatable about a second horizontal axis (A2) parallel to the first horizontal axis (A1), and has a vertical crank arm 544' that is biased to press horizontally against the lower end portion 543" of the swing lever 543, and a horizontal crank arm 544" that turns downward when the swing lever 543 rotates from the vertical position to the inclined position.

The Z-shaped crank member 545 is disposed pivotally on the support frame 3, is rotatable about a third horizontal axis (A3) parallel to the horizontal sliding rod 542, and has a generally horizontal crank arm 545' and an L-shaped crank arm 545" that turns upward when the horizontal crank arm 545'turns downward. The horizontal crank arm 545' is provided with a rotatable adjustment bolt 548 that is biased to press upwardly against the horizontal crank arm 544" of the L-shaped crank member 544.

The vertical link 546 has an upper end connected pivotally to an end of the L-shaped crank arm 545" of the Z-shaped crank member 545.

The swing arm 547 has an end 547' that is connected fixedly to the lower first throttle valve 531' which is in the form of an adjustment bolt that is parallel to the first and second horizontal axes (A1, A2), and a horizontal upper arm portion (547H) that is connected pivotally to a lower end of the link 546.

A coiled compression spring 549 is disposed between the support frame 3 and the horizontal upper arm portion (547H)

of the swing arm 547, and is located above the horizontal upper arm portion (547H) of the swing arm 547 so as to bias the horizontal upper arm portion (547H) of the swing arm 547 to turn downward, thereby pushing the link 546 downward. Hence, the L-shaped crank arm 545" of the Z-shaped crank member 545 turns downward such that the horizontal crank arm 545' of the Z-shaped crank member 545 turns upward to push the horizontal crank arm 544" of the L-shaped crank member 544 to turn upward so that the vertical crank arm 544' of the L-shaped crank member 544 pushes the swing lever 543 to the vertical position, thereby moving the horizontal sliding rod 542 and the controlling element 541 respectively to the non-pushing position and the extended position shown in FIGS. 11 and 12.

When the lower leg 9 is pressed against the ground by the thigh 8, the controlling element 541 is pressed by the rotatable member 12 to the retracted position shown in FIGS. 13 and 14, where the second linkage unit 54 is driven by the controlling element 541 to rotate the lower first throttle valve 531' so as to close the knee-flexing oil passage 513. As such, when the wearer walks along a sloping path, the lower leg 9 can stand stably on the ground to provide a sufficient support to the thigh 8 during flexion of the joint. At this time, the thigh 8 cannot rotate relative to the lower leg 9 in view of the fact that the lower first throttle valve 531' stops the oil flow through the knee-flexing oil passage 513.

The upper first throttle valve 531 and the throttle valve 531" of the adjustment unit 53 are provided for manual adjustment.

Referring to FIGS. 5, 7, 7A, and 15, upon fast walking of the wearer, an air valve unit 6 activates the swing arm 457 so as to rotate the lower first throttle valve 531' in a predetermined direction, thereby reducing oil flow through the knee-flexing oil passage 513. The air valve unit 6 includes a vertical cylindrical valve seat 61 disposed in the support frame 3 under the piston rod 421 and having an open lower end for introduction of air from the ambient. A third unidirectional valve 62 is disposed within the lower end of the valve seat 61 for limiting air flow from the ambient into the valve seat 61. A coiled compression spring 63 is disposed between the lower end of the piston rod 421 and the valve seat 61. An air passage unit is formed in the support frame 3, is in fluid communication with the upper end of the valve seat 61, and includes the air passage 519 in the main body 51 and an air passage 60 that is formed in the piston rod 421 and that is in fluid communication with the upper end of the valve seat 61 and the air inlet 517 of the air passage 519. Air is introduced into the support frame 3 through the lower end of the valve seat 61, and is discharged from the main body 51 through the air outlet 518.

A spring-biased check valve 64 is disposed within the air inlet 517 in the main body 51 for preventing air flow from the air passage 519 in the main body 51 into the air inlet 517 and for permitting air flow from the air inlet 517 into the air passage 519 in the main body 51 when air pressure in the air inlet 517 is above a first predetermined pressure that can be adjusted by rotating an adjustment bolt 66.

Figure 7:
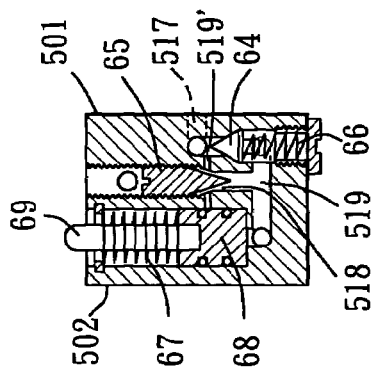
FIG. 7 is a sectional view of the main body of the preferred embodiment, taken along line VII—VII in FIG. 5.
Figure 7A:
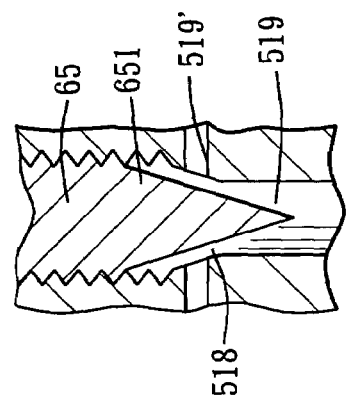
FIG. 7A is a schematic fragmentary sectional view of the preferred embodiment, illustrating how a second throttle valve is disposed within an air outlet in the main body.

A second throttle valve 65 is disposed within the air outlet 518, and is adjustable to change flow rate of air flowing through the air outlet 518. The air outlet 518 is circular. The second throttle valve 65 is configured as an adjustment bolt that has a tapered end 651 which extends into the air outlet 518 and which is movable relative to the air outlet 518 so as to change the area of an annular space between the tapered end 651 and a wall 519' defining the air outlet 518, as shown in FIG. 7A.

A rod-receiving chamber 67 is formed in the main body 51, and is adjacent to and is in fluid communication with the air passage 519. A sliding member 68 is disposed movably and sealingly in the rod-receiving chamber 67, and can be moved by air within the air passage 519 in the main body 51 when air pressure in the air passage 519 in the main body 51 is above a second predetermined pressure.

A spring-biased push rod 69 is disposed within the main body 51, is connected fixedly to the sliding member 68, and is biased to separate from an inclined arm portion (547D) of the swing arm 547. The push rod 69 is driven by air in the air passage 519 to press against the inclined arm portion (547D) of the swing arm 547 so as to rotate the swing arm 547 in the predetermined direction in response to fast walking of the wearer, thereby reducing the flex angle of the joint during flexion of the joint, i.e. the rotational angle of the lower leg 9 relative to the thigh 8.

Due to the presence of the safety device 5 and the air valve unit 6, the multi-functional artificial joint of this invention enables the wearer to walk fast and run along a sloping path in a steady manner.

With this invention thus explained, it is apparent that numerous modifications and variations can be made without departing from the scope and spirit of this invention. It is therefore intended that this invention be limited only as indicated by the appended claims.

We claim:

1. A multi-functional artificial knee joint for connecting a prosthetic lower leg to a residual thigh of a prosthesis wearer, comprising:
   a joint seat having a joint body and a rotatable member that is connected pivotally to said joint body and that is adapted to be mounted to the thigh;
   a hollow support frame connected pivotally to said joint body;
   a first linkage unit connected to said support frame and said joint body;
   a hydraulic device disposed within said support frame and including a cylinder body, a piston rod, and a piston connected fixedly to said piston rod and disposed slidably within said cylinder body so as to divide an interior space in said cylinder body into an upper oil chamber and a lower oil chamber, said piston being driven by said first linkage unit to move within said cylinder body between an upper limit position and a lower limit position, said piston moving from said upper limit position to said lower limit position when said joint flexes to form an angle between the thigh and the lower leg, said piston moving from said lower limit position to said upper limit position when said joint extends to align the thigh with the lower leg;
   a safety device including
      a main body having a knee-flexing oil passage in fluid communication with said upper and lower oil chambers, and a knee-extending oil passage in fluid communication with said upper and lower oil chambers,
      a control valve unit for closing said knee-flexing oil passage during movement of said piston from said upper limit position to said lower limit position so as to permit oil flow from said lower oil chamber into said upper oil chamber through said knee-flexing oil passage, and for closing said knee-extending oil passage during movement of said piston from said lower limit position to said upper limit position so as to permit oil flow from said upper oil chamber into said lower oil chamber through said knee-extending oil passage, a first throttle valve disposed in said knee-flexing oil passage, and a controlling element disposed movably on said support frame and connected operatively to said first throttle valve, said controlling element being driven by said rotatable member to move relative to said support frame to activate said first throttle valve so as to stop oil flow through said knee-flexing oil passage, thereby fixing the thigh relative to the lower leg when the lower leg is pressed against the ground by the thigh; and an air valve unit disposed on said support frame and connected operatively to said first throttle valve, said air valve unit activating said first throttle valve to reduce flow rate of oil flowing through said knee-flexing oil passage in response to fast walking of the prosthesis wearer.

2. The multi-functional artificial knee joint as claimed in claim 1, wherein said control valve unit includes a first unidirectional valve disposed in said knee-extending oil passage for preventing oil flow from said lower oil chamber into said upper oil chamber through said knee-extending oil passage and for permitting oil flow from said upper oil chamber into said lower oil chamber through said knee-extending oil passage, and a second unidirectional valve disposed in said knee-flexing oil passage for preventing oil flow from said upper oil chamber into said lower oil chamber through said knee-flexing oil passage and for permitting oil flow from said lower oil chamber into said upper oil chamber through said knee-flexing oil passage.

3. The multi-functional artificial knee joint as claimed in claim 1, wherein said controlling element is movable between an extended position, where said controlling element projects from said support frame, and a retracted position, where said controlling element is retracted into said support frame, said controlling element being biased to said extended position when the lower leg is not pressed against the ground by the thigh, said rotatable member being rotatable relative to said support frame to push said controlling element to said retracted position when the lower leg is pressed against the ground by the thigh.

4. The multi-functional artificial knee joint as claimed in claim 1, wherein said first throttle valve is configured as an adjustment bolt that is rotatable relative to said main body of said safety device to extend into said knee-flexing oil passage, said safety device further including a second linkage unit that connects said controlling element to said first throttle valve and that activates said first throttle valve to stop oil flow through said knee-flexing oil passage when said controlling element moves to said retracted position.

5. The multi-functional artificial knee joint as claimed in claim 4, wherein said controlling element is configured as a vertical sliding rod that is guided to move along a longitudinal direction of said support frame and that has an inclined lower end surface, said second linkage unit including:

a horizontal sliding rod disposed movably within said support frame and having an outer end and an inclined inner end surface that is biased to press horizontally against and that is slidable on said inclined lower end surface of said controlling element, said horizontal sliding rod being guided to move along a transverse direction of said support frame between a non-pushing position, where said controlling element is disposed at said extended position, and a pushing position, where said controlling element is disposed at said retracted position;

a vertical swing lever having a middle portion that is mounted pivotally on said support frame, an upper end portion that is biased to press against said outer end of said horizontal sliding rod, and a lower end portion, said swing lever being rotatable about a first horizontal axis between a vertical position, where said horizontal sliding rod is disposed at said non-pushing position, and an inclined position, where said horizontal sliding rod is disposed at said pushing position, said first horizontal axis being perpendicular to said controlling element and said horizontal sliding rod;

a generally L-shaped crank member mounted pivotally on said support frame and rotatable about a second horizontal axis parallel to said first horizontal axis, said L-shaped crank member having a vertical crank arm that is biased to press horizontally against said lower end portion of said swing lever, and a horizontal crank arm that turns downward when said swing lever rotates from said vertical position to said inclined position;

a generally Z-shaped crank member disposed pivotally on said support frame and rotatable about a third horizontal axis that is parallel to said horizontal sliding rod, said Z-shaped crank member having a generally horizontal crank arm that is biased to press upwardly against said horizontal crank arm of said L-shaped crank member, and an L-shaped crank arm that turns upward when said horizontal crank arm turns downward;

a vertical link having an upper end connected pivotally to an end of said L-shaped crank arm of said Z-shaped crank member, and a lower end; and a swing arm having an end that is connected fixedly to said adjustment bolt, and a horizontal upper arm portion that is connected pivotally to said lower end of said link, said adjustment bolt being parallel to said first and second horizontal axes and being driven by said second linkage unit to close said knee-flexing oil passage when said controlling element is disposed at said retracted position, said swing arm being connected to said air valve unit so that said air valve unit can rotate said adjustment bolt in a predetermined direction, thereby reducing the flow rate of the oil flowing through said knee-flexing oil passage.

6. The multi-functional artificial knee joint as claimed in claim 5, wherein said second linkage unit further includes a coiled compression spring that is disposed between said support frame and said horizontal upper arm portion of said swing arm and that is located above said horizontal upper arm portion of said swing arm so as to bias said horizontal upper arm portion of said swing arm to turn downward, thereby pushing said link downward, which in turn turns said L-shaped crank arm of said Z-shaped crank member downward such that said horizontal crank arm of said Z-shaped crank member turns upward to push said horizontal crank arm of said L-shaped crank member to turn upward so that said vertical crank arm of said L-shaped crank member pushes said swing lever to said vertical position, thereby moving said horizontal sliding rod and said controlling element respectively to said non-pushing position and said extended position.

7. The multi-functional artificial knee joint as claimed in claim 5, wherein said swing arm further has an inclined arm portion, said air valve unit including:

a vertical cylindrical valve seat disposed in said support frame under said piston rod and having a lower end for introduction of air from ambient, and an upper end;

a third unidirectional valve disposed within said lower end of said valve seat for limiting air flow from the ambient into said valve seat;

an air passage unit formed in said support frame and in fluid communication with said upper end of said valve seat, said air passage unit having an outlet that is adapted to discharge air from said air passage unit into the ambient therethrough; and a spring-biased push rod disposed within said support frame and biased to separate from said swing arm, said push rod being driven by air in said air passage unit to press against said inclined arm portion of said swing arm so as to rotate said swing arm in said predetermined direction in response to fast walking of the wearer.

8. The multi-functional artificial knee joint as claimed in claim 7, wherein said piston rod is formed with an air passage, said main body further having an air inlet, an air outlet constituting said outlet of said air passage unit, and an air passage in fluid communication with said air inlet and said air outlet, said air passages in said piston rod and said main body being in fluid communication with each other and constituting cooperatively said air passage unit, said main body including:

a spring-biased check valve disposed within said air inlet in said main body for preventing air flow from said air passage in said main body into said air inlet and for permitting air flow from said air inlet into said air passage in said main body when air pressure in said air inlet is above a first predetermined pressure;

a second throttle valve disposed within said air outlet and adjustable to change flow rate of air flowing through said air outlet;

a rod-receiving chamber disposed adjacent to and in fluid communication with said air passage in said main body;

a sliding member disposed movably and sealingly in said rod-receiving chamber and connected fixedly to said push rod, said sliding member being moved by air within said air passage in said main body when air pressure in said air passage in said main body is above a second predetermined pressure.

* * * * *